(12) United States Patent
Weiss et al.

(10) Patent No.: US 7,125,684 B2
(45) Date of Patent: Oct. 24, 2006

(54) HUMAN MATER PROTEINS

(75) Inventors: Bertram Weiss, Berlin (DE); Monika Lessl, Gienicke-Nordbahn (DE); Michaele Peters-Kottig, Berlin (DE); Georg Beckmann, Berlin (DE)

(73) Assignee: Schering AG, Berlin (DE)

( * ) Notice: Subject to any disclaimer, the term of this patent is extended or adjusted under 35 U.S.C. 154(b) by 399 days.

(21) Appl. No.: 10/216,645

(22) Filed: Aug. 12, 2002

(65) Prior Publication Data

US 2003/0125282 A1    Jul. 3, 2003

(30) Foreign Application Priority Data

Aug. 10, 2001 (DE) ................. 101 39 874

(51) Int. Cl.
*C12Q 1/42* (2006.01)
*C12N 9/14* (2006.01)

(52) U.S. Cl. ........................... 435/21; 435/195

(58) Field of Classification Search ........... 530/350; 435/7.1, 21, 199
See application file for complete search history.

(56) References Cited

U.S. PATENT DOCUMENTS

| 2004/0028669 A1* | 2/2004 | Nelson et al. ............ 424/94.1 |
| 2004/0043452 A1* | 3/2004 | Ramkumar et al. ........ 430/69.1 |

FOREIGN PATENT DOCUMENTS

| WO | WO 02/32955 A1 | 4/2002 |
| WO | WO 0240668 | 5/2002 |

OTHER PUBLICATIONS

Tong et al. Mater, a maternal effect gene required for early embryonic development in mice. Nature Genetics, 2000, V26, N3 (Nov.), p. 267-268.*
Tschopp et al. "NALPs : a novel protein family involved in inflammation." Nature reviews. Molecular cell biology (England) Feb. 2003, 4 (2) p. 95-104.*
M.H. Melner et al., "Editorial: Auoimmune Premature Ovarian Failure-Endocrine Aspects of a T cell Disease," ENDOCRINOLOGY, Baltimore, Md., U.S., Bd. 140, Nr. 8, 1999, pp. 3401-3403, XP002181744.
Zhi-Bin Tong et al., "A Mouse Gene Encoding an Oocyte Antigen Associated with Autoimmune Premature Ovarian Failure," ENDOCRINOLOGY, Baltimore, Md., U.S., Bd. 140, Nr. 8, Aug. 1999, pp. 3720-3726, XP002181743.
Zhi-Bin Tong et al., "Mater Encodes a Maternal Protein In Mice With A Leucine-Rich Repeat Domain Homologous to Porcine Ribonuclease Inhibitor," Mammalian Genome, NY, NY Bd. 11, Nr. 4, pp. 281-287, Apr. 2000, XP001035150.
Verhage et al. "Characteristics of an Oviductal Glycoprotein and its Potential Role in Fertility Control" in *Reproduction in Dogs, Cats and Exotic Carnivores*, Concannon et al, eds. J. Reproduction & Fertility, Supp. 51 217-226 1997.
Zhi-Bin Tong et al., "A human homologue of a mouse Mater, a maternal effect gene essential for early embryonic development", Human Reproduction vol. 17, No. 4, pp. 903-911, 2002.
NCBI Genbank sequence disclosure, "*Homo sapiens*", Accession No. NM 153447.1 GI: 23592233, (the reference sequence was derived from AY054986.1), Bethesda Md, National Library of Medicine 2002.
The DAPIN faimly: a novel domain links apoptotic and interferon response proteins; Eike Staub et al.; XP-002212416.

* cited by examiner

*Primary Examiner*—Gabriele Bugaisky
(74) *Attorney, Agent, or Firm*—Millen, White, Zelano & Branigan

(57) ABSTRACT

Two human MATER proteins as well as their use for fertility disorders, therapy and diagnosis are described.

9 Claims, 6 Drawing Sheets

```
mmMater   ---------------MGPPEKESKAILKARGLEEEQKSERKMTSP---ENDSKSIQKDQG
hs_mater  MEGDKSLTFSSYGLQWCLYEDDKEEQTWELEKKKSSESTTCSIPQFETENANVECLAL    DAPIN/PAAD
                         *  :.:  :  .  :  *  :::.**  .  *      *  :.  .::

mmMater   PEQEQTSESTMGPPEKDSKAILKARGLEEEQKSESTMSPSENVSRAILKDSG-SEEVEQA
hs_mater  LLHEYGGASLAWATSISIFENMNLRTLGEKARDDMKNSPED--PEATMTDQGPSKEKVPE
          :*  . *   ...  .   :: * *.*: :.: . **.:  ..* :.*.* *;* mmMater   SERKMT------SPENDSKSIQK----------DCGPEQE-------QTSETLQSKEED
hs_mater  NKYGMTKLILGVSDISDSNNKHKYVGIHSSFAEISQAMEQEGATAAETEEQEISQAMEQE
          .:   **       * .**:. :*          .*. ***        : .*  *: *::

mmMater   EVTEADKD---NGGDLQDYKAHVIAKFDTSVDLHY-------DSPEMKLLSDAFKPYQKT
hs_mater  GATAAETEEQGHGGDTWDYKSHVMTKFAEEEDVRRSFENTAADWPEMQTLAGAFDSDRWG
          .* *:.:    :*** ***:**:.**   .*::         * ***:  *:.**.. :

mmMater   FQPHTIILHGRPGVGKSALARSIVLGWAQGKLFQ-KMSFVIFFSVREIKWTEKSSLAQLI
hs_mater  FRPRTVVLHGKSGIGKSALARRIVLCWAQGGLYQGMFSYVFFLPVREMQRKKESSVTEFI mmMater   AKECPDSWDLVTKIMSQPERLLFVIDGLDDMDSVLQHDDMTLSRDWKDEQPIYILMYSLL
hs_mater  SREWPDSQAPVTEIMSRPERLLFIIDGPDDLGSVLN-NDTKLCKDWAEKQPPFTLIRSLL mmMater   RKALLPQSFLIITTRNTGLEKLKSMVVSPLYILVEGLSASRRSQLVLENISNESDRIQVF
hs_mater  RKVLLPESFLIVTVRDVGTEKLKSEVVSPRYLLVRGISGEQRIHDLLERGIGEHQKTQGL    NACHT domain mmMater   HSLIENHQLFDQCQAPSVCSLVCEALQLQKKLGKRCTLPCQTLTGLYATLVFHQLTLKRP
hs_mater  RAIMNNRELLDQCQVPAVGSLICVALQLQDVVGESVAPFNQTLTGLHAAFVEHQLTPRGV mmMater   SQSALSQEEQITLVGLCMMAAEGVWTMRSVFYDDDLKNYSLKESEILALFHMNILLQVGH
hs_mater  VRRCLNLEERVVLKRFCRMAVEGVWNRKSVFDGDDLMVQCLGESELRALFHMNILLPDSH mmMater   NSEQCYVFSHLSLQDFFAALYYVLEGLEEWNQHF-C...
hs_mater  CEEYYTFFHLSLQDFCAALYYVLEGLEIEPALCPL...
```

FIGURE 1a

```
mmMater    [shaded]
hs_mater   [shaded]                                                       DUF mmMater    [shaded]
hs_mater   [shaded]

mmMater    [shaded]CKPLLMEWWGNFCSVLGSLRNLKELDLGDSILSQRAMKILCLELRNQSCRIQ
hs_mater   [shaded]-KTLIEEQWEDFCSMLGTHPHLRQLDLGSSILTERAMKTLCAKLRHPTCKIQ    LRRs
           [shaded] *.*:  * *  :***:**:     .:.****.***.:****.*  :**: .*:**

mmMater    KLTFKSAEVVSGLKHLWKLLFSNQNLKYLNLGNTPMKDDDMKLACEALKHPKCSVETLRL
hs_mater   TLMFRNAQITPGVQHLWRIVMANRNLRSLNLGGTHLKEEDVRMACEALKHPKCLLESLRL
           .*.*:.*:: .*::**:**:::.:*:*:*.****..*: *::*:.**********:*.:**

mmMater    DSCELTIIGYEMISTLLISTTRLKCLSLAKNRVGVKSMISLGNALSSSMCLLQKLILDNC
hs_mater   DCCGLTHACYLKISQILTTSPSLKSLSLAGNKVTDQGVMPLSDALRVSQCALQKLILEDC
           *.*    :::*.:*::.  .**.*:*. :.:.*..   *.*****::* mmMater    GLTPASCHLLVSALFSNQNLTHLCLSNNSLGTEGVQQLCQFLRNPECALQRLILNHCNIV
hs_mater   GITATGCQSLASALVSNRSLTHLCLSNNSLGNEGVNLLCRSMRLPHCSLQRLMLNQCHLD
           *:*. .*:.*.*.:.********.*  **:. * *:*:**::* mmMater    DDAYGFLAMRLANNTKLTHLSLTMNPVGDGAMKLLCEALKEPTCYLQELELVDCQLTQNC
hs_mater   TAGCGFLALALMGNSWLTHLSLSMNPVEDNGVKLLCEVMREPSCHLQDLELVKCHLTAAC
            ..****: * . *: *****:**.*.. **. ::*::**.*.**..* mmMater    CEDLACMITTTKHLKSLDLGNNALGDKGVITLCEGLKQSSSSLRRLGLGACKLTSNCCEA
hs_mater   CESLSCVISRSRHLKSLDLTDNALGDGGVAALCEGLKQNSVLTRLGLKACGLTSDCCEA
           **.*:*:*: ::*******..*****.**:: ******.*. *:****.**.***:****

mmMater    LSLAISCNPHLNSLNLVKNDFSTSGMLKLCSAFQCPVSNLGIIGLWKQEYYARVRRQLEE
hs_mater   LSLALSCNRHLTSLNLVQNNFSPKGMMKLCSAFACPTSNLQIIGLWKQYPVQIRKLLEE
           ****:***:**.*****:*:**..**:***** **.***:*******:  . :*:*:**

mmMater    VEFVKPHVVIDGDWYASDEDDRNWWKN
hs_mater   VQLLKPRVVIDGSWHSFDEDDRYWWKN
           *:::** :****.* :  ******.****
```

FIGURE 1b

| Domain | sub# | Amino acids from | to |
|---|---|---|---|
| Dapin domain | | 1 | 92 |
| NACHT domain | | 243 | 563 |
| DUF | | 570 | 720 |
| LRR | 1/14 | 745 | 763 |
| LRR | 2/14 | 774 | 791 |
| LRR | 3/14 | 801 | 816 |
| LRR | 4/14 | 830 | 848 |
| LRR | 5/14 | 858 | 876 |
| LRR | 6/14 | 888 | 905 |
| LRR | 7/14 | 915 | 930 |
| LRR | 8/14 | 944 | 962 |
| LRR | 9/14 | 972 | 989 |
| LRR | 10/14 | 1001 | 1019 |
| LRR | 11/14 | 1029 | 1047 |
| LRR | 12/14 | 1058 | 1076 |
| LRR | 13/14 | 1086 | 1103 |
| LRR | 14/14 | 1115 | 1133 |

FIGURE 2

LH+4: before opening of implantation window
LH+8: implantation window is open, healthy young women
LH+8 EMT: implantation window is open, women suffering from endometriosis Numbers on the x-axsis: patient numbers

SEQUENCE LISTING

<160> NUMBER OF SEQ ID NOS: 11

<210> SEQ ID NO 1
<211> LENGTH: 3926
<212> TYPE: DNA
<213> ORGANISM: Homo sapiens

<400> SEQUENCE: 1
atggaaggag acaaatcgct caccttttcc agctacgggc tgcaatggtg tctctatgag        60

-continued

```
ctagacaagg aagaatttca gacattcaag gaattactaa agaagaaatc ttcagaatcg      120
accacatgct ctattccaca gtttgaaatc gagaatgcca acgtggaatg tctggcactc      180
ctcttgcatg agtattatgg agcatcgctg gcctgggcta cgtccattag catctttgaa      240
aacatgaacc tgcgaaccct ctcggagaag gcacgggatg acatgaaaaa ttcaccagaa      300
gatcctgaag caacgatgac tgaccaagga ccaagcaagg aaaaagtgcc agaaaataaa      360
tatggcatga ctaagcttat cttggggtg tctgacatct ctgactcgaa taataaacac       420
aagtatgttg gaattcattc ttcttttgca gaaatttcac aagctatgga acaagaaggt      480
gccacagcag cagagacaga agaacaagaa atttcacaag ctatggaaca agaaggtgcc      540
acagcagcag agacagaaga acaaggacat ggaggtgaca catgggacta caagagtcac      600
gtgatgacca aattcgctga ggaggaggat gtacgtcgta gttttgaaaa cactgctgct      660
gactggccgg aaatgcaaac gttggctggt gcttttgatt cagaccggtg gggcttccgg      720
cctcgcacgg tggttctgca cggaaagtca ggaattggga atcggctct agccagaagg       780 atcgtgctgt gctgggcgca aggtggactc taccagggaa tgttctccta cgtcttcttc      840
ctccccgtta gagagatgca gcggaagaag gagagcagtg tcacagagtt catctccagg      900
gagtggccag actccaggc tccggtgacg gagatcatgt cccgaccaga aaggctgttg       960
ttcatcattg acggtttcga tgacctgggc tctgtcctca caatgacac aaagctctgc      1020 aaagactggg ctgagaagca gcctccgttc accctcatac gcagtctgct gaggaaggtc      1080
ctgctccctg agtccttcct gatcgtcacc gtcagagacg tgggcacaga gaagctcaag     1140
tcagaggtcg tgtctccccg ttacctgtta gttagaggaa tctccgggga acaaagaatc     1200
cacttgctcc ttgagcgcgg gattggtgag catcagaaga cacaagggtt gcgtgcgatc     1260
atgaacaacc gtgagctgct cgaccagtgc caggtgcccg ccgtgggctc tctcatctgc     1320
gtggccctgc agctgcagga cgtggtgggg gagagcgtcg ccccccttcaa ccaaacgctc    1380 acaggcctgc acgccgcttt tgtgtttcat cagctcaccc ctcgaggcgt ggtccggcgc     1440
tgtctcaatc tggaggaaag agttgtcctg aagcgcttct gccgtatggc tgtggaggga    1500
gtgtggaata ggaagtcagt gtttgacggt gacgacctca tggttcaagg actcggggag     1560
tctgagctcc gtgctctgtt tcacatgaac atccttctcc cagacagcca ctgtgaggag     1620 tactacaccct tcttccacct cagtctccag gacttctgtg ccgccttgta ctacgtgtta    1680
gagggcctgg aaatcgagcc agctctctgc cctctgtacg ttgagaagac aaagaggtcc     1740
atggagctta acaggcagg cttccatatc cactcgcttt ggatgaagcg tttcttgttt      1800
ggcctcgtga gcgaagacgt aaggaggcca ctggaggtcc tgctgggctg tcccgttccc     1860
ctgggggtga agcagaagct tctgcactgg gtctctctgt tgggtcagca gcctaatgcc     1920
accaccccag gagacaccct ggacgccttc cactgtcttt tcgagactca agacaaagag     1980
tttgttcgct tggcattaaa cagcttccaa gaagtgtggc ttccgattaa ccagaacctg     2040
gacttgatag catcttcctt ctgcctccag cactgtccgt atttgcggaa aattcgggtg     2100
gatgtcaaag ggatcttccc aagagatgag tccgctgagg catgtcctgt ggtccctcta     2160
tggatgcggg ataagaccct cattgaggag cagtgggaag atttctgctc catgcttggc     2220
acccacccac acctgcggca gctggacctg ggcagcagca tcctgacaga gcgggccatg     2280
aagaccctgt gtgccaagct gaggcatccc acctgcaaga tacagaccct gatgtttaga     2340
aatgcacaga ttaccccctgg tgtgcagcac ctctggagaa tcgtcatggc caaccgtaac     2400
```

-continued

```
ctaagatccc tcaacttggg aggcacccac ctgaaggaag aggatgtaag gatggcgtgt    2460
gaagccttaa acacccaaa atgtttgttg gagtctttga ggctggattg ctgtggattg    2520
acccatgcct gttacctgaa gatctcccaa atccttacga cctcccccag cctgaaatct    2580
ctgagcctgg caggaaacaa ggtgacagac cagggagtaa tgcctctcag tgatgccttg    2640
agagtctccc agtgcgccct gcagaagctg atactggagg actgtggcat cacagccacg    2700
ggttgccaga gtctggcctc agccctcgtc agcaaccgga gcttgacaca cctgtgccta    2760
tccaacaaca gcctggggaa cgaaggtgta aatctactgt gtcgatccat gaggcttccc    2820
cactgtagtc tgcagaggct gatgctgaat cagtgccacc tggacacggc tggctgtggt    2880
tttcttgcac ttgcgcttat gggtaactca tggctgacgc acctgagcct tagcatgaac    2940
cctgtggaag acaatggcgt gaagcttctg tgcgaggtca tgagagaacc atcttgtcat    3000
ctccaggacc tggagttggt aaagtgtcat ctcaccgccg cgtgctgtga gagtctgtcc    3060
tgtgtgatct cgaggagcag acacctgaag agcctggatc tcacgacaa tgccctgggt    3120 gacggtgggg ttgctgcact gtgcgaggga ctgaagcaaa agaacagtgt tctgacgaga    3180
ctcgggttga aggcatgtgg actgacttct gattgctgtg aggcactctc cttggccctt    3240
tcctgcaacc ggcatctgac cagtctaaac ctggtgcaga ataacttcag tcccaaagga    3300
atgatgaagc tgtgttcggc ctttgcctgt cccacgtcta acttacagat aattgggctg    3360
tggaaatggc agtaccctgt gcaaataagg aagctgctgg aggaagtgca gctactcaag    3420
ccccgagtcg taattgacgg tagttggcat tcttttgatg aagatgaccg gtactggtgg    3480
aaaaactgaa gatacggaaa cctgccccac tcacacccat ctgatggagg aactttaaac    3540
gctgttttct cagagcaagc tatgcacctg ggagttcctt ctcaaagatg gagaatgatt    3600
tctgattctc acaaagccct caatggtagt gattcttctg tgttcactct acgttggtta    3660
ctggatttga aggctagaga ccttcaagtc ataggactca gtatctgtga aatgtccgtc    3720
atatctcaga gcatatagag ggaattaaat aaacacaaag catttggaaa agttgtcaag    3780
tggttttctt aactagtgga gatatggttt aggagcagag aggttgggag gacctagatc    3840
ttcaaaagaa gccctgaat ttgggtacca caactagtgg tggtttttg ttttttgtgt    3900 ttttcttttt gttttttggt tttttt                                        3926
```

<210> SEQ ID NO 2
<211> LENGTH: 1162
<212> TYPE: PRT
<213> ORGANISM: Homo sapiens

<400> SEQUENCE: 2

```
Met Glu Gly Asp Lys Ser Leu Thr Phe Ser Ser Tyr Gly Leu Gln Trp
  1               5                  10                  15

Cys Leu Tyr Glu Leu Asp Lys Glu Glu Phe Gln Thr Phe Lys Glu Leu
                 20                  25                  30

Leu Lys Lys Lys Ser Ser Glu Ser Thr Thr Cys Ser Ile Pro Gln Phe
             35                  40                  45

Glu Ile Glu Asn Ala Asn Val Glu Cys Leu Ala Leu Leu His Glu
         50                  55                  60

Tyr Tyr Gly Ala Ser Leu Ala Trp Ala Thr Ser Ile Ser Ile Phe Glu
 65                  70                  75                  80

Asn Met Asn Leu Arg Thr Leu Ser Glu Lys Ala Arg Asp Asp Met Lys
                 85                  90                  95

Asn Ser Pro Glu Asp Pro Glu Ala Thr Met Thr Asp Gln Gly Pro Ser
```

-continued

```
            100                 105                 110
Lys Glu Lys Val Pro Glu Asn Lys Tyr Gly Met Thr Lys Leu Ile Leu
            115                 120                 125
Gly Val Ser Asp Ile Ser Asp Ser Asn Asn Lys His Lys Tyr Val Gly
        130                 135                 140
Ile His Ser Ser Phe Ala Glu Ile Ser Gln Ala Met Glu Gln Glu Gly
145                 150                 155                 160
Ala Thr Ala Ala Glu Thr Glu Gln Glu Ile Ser Gln Ala Met Glu
                165                 170                 175
Gln Glu Gly Ala Thr Ala Ala Glu Thr Glu Gln Gly His Gly Gly
            180                 185                 190
Asp Thr Trp Asp Tyr Lys Ser His Val Met Thr Lys Phe Ala Glu Glu
            195                 200                 205
Glu Asp Val Arg Arg Ser Phe Glu Asn Thr Ala Ala Asp Trp Pro Glu
        210                 215                 220
Met Gln Thr Leu Ala Gly Ala Phe Asp Ser Asp Arg Trp Gly Phe Arg
225                 230                 235                 240
Pro Arg Thr Val Val Leu His Gly Lys Ser Gly Ile Gly Lys Ser Ala
                245                 250                 255
Leu Ala Arg Arg Ile Val Leu Cys Trp Ala Gln Gly Gly Leu Tyr Gln
            260                 265                 270
Gly Met Phe Ser Tyr Val Phe Leu Pro Val Arg Glu Met Gln Arg
        275                 280                 285
Lys Lys Glu Ser Ser Val Thr Glu Phe Ile Ser Arg Glu Trp Pro Asp
        290                 295                 300
Ser Gln Ala Pro Val Thr Glu Ile Met Ser Arg Pro Glu Arg Leu Leu
305                 310                 315                 320
Phe Ile Ile Asp Gly Phe Asp Leu Gly Ser Val Leu Asn Asn Asp
                325                 330                 335
Thr Lys Leu Cys Lys Asp Trp Ala Glu Lys Gln Pro Phe Thr Leu
            340                 345                 350
Ile Arg Ser Leu Leu Arg Lys Val Leu Leu Pro Glu Ser Phe Leu Ile
        355                 360                 365
Val Thr Val Arg Asp Val Gly Thr Glu Lys Leu Lys Ser Glu Val Val
370                 375                 380
Ser Pro Arg Tyr Leu Leu Val Arg Gly Ile Ser Gly Glu Gln Arg Ile
385                 390                 395                 400
His Leu Leu Leu Glu Arg Gly Ile Gly Glu His Gln Lys Thr Gln Gly
                405                 410                 415
Leu Arg Ala Ile Met Asn Asn Arg Glu Leu Leu Asp Gln Cys Gln Val
            420                 425                 430
Pro Ala Val Gly Ser Leu Ile Cys Val Ala Leu Gln Leu Gln Asp Val
        435                 440                 445
Val Gly Glu Ser Val Ala Pro Phe Asn Gln Thr Leu Thr Gly Leu His
        450                 455                 460
Ala Ala Phe Val Phe His Gln Leu Thr Pro Arg Gly Val Val Arg Arg
465                 470                 475                 480
Cys Leu Asn Leu Glu Glu Arg Val Val Leu Lys Arg Phe Cys Arg Met
                485                 490                 495
Ala Val Glu Gly Val Trp Asn Arg Lys Ser Val Phe Asp Gly Asp Asp
            500                 505                 510
Leu Met Val Gln Gly Leu Gly Glu Ser Glu Leu Arg Ala Leu Phe His
            515                 520                 525
```

-continued

```
Met Asn Ile Leu Leu Pro Asp Ser His Cys Glu Glu Tyr Tyr Thr Phe
        530                 535                 540
Phe His Leu Ser Leu Gln Asp Phe Cys Ala Ala Leu Tyr Tyr Val Leu
545                 550                 555                 560
Glu Gly Leu Glu Ile Glu Pro Ala Leu Cys Pro Leu Tyr Val Glu Lys
                565                 570                 575
Thr Lys Arg Ser Met Glu Leu Lys Gln Ala Gly Phe His Ile His Ser
        580                 585                 590
Leu Trp Met Lys Arg Phe Leu Phe Gly Leu Val Ser Glu Asp Val Arg
        595                 600                 605
Arg Pro Leu Glu Val Leu Leu Gly Cys Pro Val Pro Leu Gly Val Lys
        610                 615                 620
Gln Lys Leu Leu His Trp Val Ser Leu Leu Gly Gln Gln Pro Asn Ala
625                 630                 635                 640
Thr Thr Pro Gly Asp Thr Leu Asp Ala Phe His Cys Leu Phe Glu Thr
                645                 650                 655
Gln Asp Lys Glu Phe Val Arg Leu Ala Leu Asn Ser Phe Gln Glu Val
        660                 665                 670
Trp Leu Pro Ile Asn Gln Asn Leu Asp Leu Ile Ala Ser Ser Phe Cys
        675                 680                 685
Leu Gln His Cys Pro Tyr Leu Arg Lys Ile Arg Val Asp Val Lys Gly
690                 695                 700
Ile Phe Pro Arg Asp Glu Ser Ala Glu Ala Cys Pro Val Val Pro Leu
705                 710                 715                 720
Trp Met Arg Asp Lys Thr Leu Ile Glu Glu Gln Trp Glu Asp Phe Cys
                725                 730                 735
Ser Met Leu Gly Thr His Pro His Leu Arg Gln Leu Asp Leu Gly Ser
        740                 745                 750
Ser Ile Leu Thr Glu Arg Ala Met Lys Thr Leu Cys Ala Lys Leu Arg
        755                 760                 765
His Pro Thr Cys Lys Ile Gln Thr Leu Met Phe Arg Asn Ala Gln Ile
770                 775                 780
Thr Pro Gly Val Gln His Leu Trp Arg Ile Val Met Ala Asn Arg Asn
785                 790                 795                 800
Leu Arg Ser Leu Asn Leu Gly Gly Thr His Leu Lys Glu Glu Asp Val
                805                 810                 815
Arg Met Ala Cys Glu Ala Leu Lys His Pro Lys Cys Leu Leu Glu Ser
                820                 825                 830
Leu Arg Leu Asp Cys Cys Gly Leu Thr His Ala Cys Tyr Leu Lys Ile
        835                 840                 845
Ser Gln Ile Leu Thr Thr Ser Pro Ser Leu Lys Ser Leu Ser Leu Ala
850                 855                 860
Gly Asn Lys Val Thr Asp Gln Gly Val Met Pro Leu Ser Asp Ala Leu
865                 870                 875                 880
Arg Val Ser Gln Cys Ala Leu Gln Lys Leu Ile Leu Glu Asp Cys Gly
                885                 890                 895
Ile Thr Ala Thr Gly Cys Gln Ser Leu Ala Ser Ala Leu Val Ser Asn
                900                 905                 910
Arg Ser Leu Thr His Leu Cys Leu Ser Asn Asn Ser Leu Gly Asn Glu
        915                 920                 925
Gly Val Asn Leu Leu Cys Arg Ser Met Arg Leu Pro His Cys Ser Leu
930                 935                 940
```

```
Gln Arg Leu Met Leu Asn Gln Cys His Leu Asp Thr Ala Gly Cys Gly
945                 950                 955                 960

Phe Leu Ala Leu Ala Leu Met Gly Asn Ser Trp Leu Thr His Leu Ser
                965                 970                 975

Leu Ser Met Asn Pro Val Glu Asn Gly Val Lys Leu Leu Cys Glu
            980                 985                 990

Val Met Arg Glu Pro Ser Cys His Leu Gln Asp Leu Glu Leu Val Lys
        995                 1000                1005

Cys His Leu Thr Ala Ala Cys Cys Glu Ser Leu Ser Cys Val Ile Ser
    1010                1015                1020

Arg Ser Arg His Leu Lys Ser Leu Asp Leu Thr Asp Asn Ala Leu Gly
1025                1030                1035                1040

Asp Gly Gly Val Ala Ala Leu Cys Glu Gly Leu Lys Gln Lys Asn Ser
                1045                1050                1055

Val Leu Thr Arg Leu Gly Leu Lys Ala Cys Gly Leu Thr Ser Asp Cys
            1060                1065                1070

Cys Glu Ala Leu Ser Leu Ala Leu Ser Cys Asn Arg His Leu Thr Ser
        1075                1080                1085

Leu Asn Leu Val Gln Asn Asn Phe Ser Pro Lys Gly Met Met Lys Leu
    1090                1095                1100

Cys Ser Ala Phe Ala Cys Pro Thr Ser Asn Leu Gln Ile Ile Gly Leu
1105                1110                1115                1120

Trp Lys Trp Gln Tyr Pro Val Gln Ile Arg Lys Leu Leu Glu Glu Val
                1125                1130                1135

Gln Leu Leu Lys Pro Arg Val Val Ile Asp Gly Ser Trp His Ser Phe
            1140                1145                1150

Asp Glu Asp Asp Arg Tyr Trp Trp Lys Asn
        1155                1160

<210> SEQ ID NO 3
<211> LENGTH: 3830
<212> TYPE: DNA
<213> ORGANISM: Homo sapiens

<400> SEQUENCE: 3
atggaaggag acaaatcgct caccttttcc agctacgggc tgcaatggtg tctctatgag      60
ctagacaagg aagaatttca gacattcaag gaattactaa agaagaaatc ttcagaatcg     120
accacatgct ctattccaca gtttgaaatc gagaatgcca acgtggaatg tctggcactc     180
ctcttgcatg agtattatgg agcatcgctg gcctgggcta cgtccattag catctttgaa     240
aacatgaacc tgcgaaccct ctcggagaag gcacgggatg acatgaaaaa ttcaccagaa     300
gatcctgaag caacgatgac tgaccaagga ccaagcaagg aaaaagtgcc agaaaataaa     360
tatggcatga ctaagcttat cttgggggtg tctgacatct ctgactcgaa taataaacac     420
aagtatgttg gaattcattc ttcttttgca gaaatttcac aagctatgga caagaaggt      480 gccacagcag cagagacaga agaacaagga catggaggtg acacatggga ctacaagagt     540
cacgtgatga ccaaattcgc tgaggaggag gatgtacgtc gtagttttga aaacactgct     600
gctgactggc cggaaatgca aacgttggct ggtgcttttg attcagaccg gtggggcttc     660
cggcctcgca cggtggttct gcacggaaag tcaggaattg ggaaatcggc tctagccaga     720
aggatcgtgc tgtgctgggc gcaaggtgga ctctaccagg aatgttctc ctacgtcttc     780 ttcctcccg ttagagagat gcagcggaag aaggagagca gtgtcacaga gttcatctcc     840
agggagtggc cagactccca ggctccggtg acggagatca tgtcccgacc agaaaggctg     900
```

```
ttgttcatca ttgacggttt cgatgacctg ggctctgtcc tcaacaatga cacaaagctc    960
tgcaaagact gggctgagaa gcagcctccg ttcacccctca tacgcagtct gctgaggaag   1020
gtcctgctcc ctgagtcctt cctgatcgtc accgtcagag acgtgggcac agagaagctc   1080
aagtcagagg tcgtgtctcc ccgttacctg ttagttagag aatctccgg ggaacaaaga    1140
atccacttgc tccttgagcg cgggattggt gagcatcaga agacacaagg gttgcgtgcg   1200
atcatgaaca accgtgagct gctcgaccag tgccaggtgc ccgccgtggg ctctctcatc   1260
tgcgtggccc tgcagctgca ggacgtggtg ggggagagcg tcgccccctt caaccaaacg   1320
ctcacaggcc tgcacgccgc ttttgtgttt catcagctca cccctcgagg cgtggtccgg   1380
cgctgtctca atctggagga aagagttgtc ctgaagcgct tctgccgtat ggctgtggag   1440
ggagtgtgga ataggaagtc agtgtttgac ggtgacgacc tcatggttca aggactcggg   1500
gagtctgagc tccgtgctct gtttcacatg aacatccttc tcccagacag ccactgtgag   1560
gagtactaca ccttcttcca cctcagtctc caggacttct gtgccgcctt gtactacgtg   1620
ttagagggcc tggaaatcga gccagctctc tgccctctgt acgttgagaa gacaaagagg   1680
tccatggagc ttaaacaggc aggcttccat atccactcgc tttggatgaa gcgtttcttg   1740
tttggcctcg tgagcgaaga cgtaaggagg ccactggagg tcctgctggg ctgtcccgtt   1800
cccctggggg tgaagcagaa gcttctgcac tgggtctctc tgttgggtca gcagcctaat   1860
gccaccaccc caggagacac cctggacgcc ttccactgtc ttttcgagac tcaagacaaa   1920
gagtttgttc gcttggcatt aaacagcttc aagaagtgt ggcttccgat taaccagaac    1980
ctggacttga tagcatcttc cttctgcctc cagcactgtc cgtatttgcg gaaaattcgg   2040
gtggatgtca aagggatctt cccaagagat gagtccgctg aggcatgtcc tgtggtccct   2100
ctatggatgc gggataagac cctcattgag gagcagtggg aagatttctg ctccatgctt   2160
ggcacccacc cacacctgcg gcagctggac ctgggcagca gcatcctgac agagcgggcc   2220
atgaagaccc tgtgtgccaa gctgaggcat cccacctgca agatacagac cctgatgttt   2280
agaaatgcac agattacccc tggtgtgcag cacctctgga gaatcgtcat ggccaaccgt   2340
aacctaagat ccctcaactt gggaggcacc cacctgaagg aagaggatgt aaggatggcg   2400
tgtgaagcct aaaacacccc aaaatgtttg ttggagtctt tgaggctgga ttgctgtgga   2460
ttgacccatg cctgttacct gaagatctcc caaatcctta cgacctcccc cagcctgaaa   2520
tctctgagcc tggcaggaaa caaggtgaca gaccagggag taatgcctct cagtgatgcc   2580
ttgagagtct cccagtgcgc cctgcagaag ctgatactgg aggactgtgg catcacagcc   2640
acgggttgcc agagtctggc ctcagccctc gtcagcaacc ggagcttgac acacctgtgc   2700
ctatccaaca acagcctggg gaacgaaggt gtaaatctac tgtgtcgatc catgaggctt   2760
ccccactgta gtctgcagag gctgatgctg aatcagtgcc acctggacac ggctggctgt   2820
ggttttcttg cacttgcgct tatgggtaac tcatggctga cgcacctgag ccttagcatg   2880
aaccctgtgg aagacaatgg cgtgaagctt ctgtgcgagg tcatgagaga accatcttgt   2940
catctccagg acctggagtt ggtaaagtgt catctcaccg ccgcgtgctg tgagagtctg   3000
tcctgtgtga tctcgaggag cagacacctg aagagcctgg atctcacgga caatgccctg   3060
ggtgacggtg gggttgctgc actgtgcgag ggactgaagc aaaagaacag tgttctgacg   3120
agactcgggt tgaaggcatg tggactgact tctgattgct gtgaggcact ctccttggcc   3180
cttttcctgca accggcatct gaccagtcta aacctggtgc agaataactt cagtcccaaa   3240
```

-continued

```
ggaatgatga agctgtgttc ggcctttgcc tgtcccacgt ctaacttaca gataattggg      3300
ctgtggaaat ggcagtaccc tgtgcaaata aggaagctgc tggaggaagt gcagctactc      3360 aagcccccgag tcgtaattga cggtagttgg cattcttttg atgaagatga ccggtactgg     3420
tggaaaaact gaagatacgg aaacctgccc cactcacacc catctgatgg aggaacttta      3480
aacgctgttt tctcagagca agctatgcac ctgggagttc cttctcaaag atggagaatg      3540
atttctgatt ctcacaaagc cctcaatggt agtgattctt ctgtgttcac tctacgttgg      3600
ttactggatt tgaaggctag agaccttcaa gtcataggac tcagtatctg tgaaatgtcc      3660
gtcatatctc agagcatata gagggaatta aataaacaca aagcatttgg aaaagttgtc      3720
aagtggtttt cttaactagt ggagatatgg tttaggagca gagaggttgg gaggacctag      3780
atcttcaaaa gaagcccctg aatttgggta ccacaactag tggtggtttt                  3830
```

<210> SEQ ID NO 4
<211> LENGTH: 1143
<212> TYPE: PRT
<213> ORGANISM: Homo sapiens

<400> SEQUENCE: 4

```
Met Glu Gly Asp Lys Ser Leu Thr Phe Ser Ser Tyr Gly Leu Gln Trp
  1               5                  10                  15

Cys Leu Tyr Glu Leu Asp Lys Glu Glu Phe Gln Thr Phe Lys Glu Leu
             20                  25                  30

Leu Lys Lys Lys Ser Ser Glu Ser Thr Thr Cys Ser Ile Pro Gln Phe
         35                  40                  45

Glu Ile Glu Asn Ala Asn Val Glu Cys Leu Ala Leu Leu His Glu
     50                  55                  60

Tyr Tyr Gly Ala Ser Leu Ala Trp Ala Thr Ser Ile Ser Ile Phe Glu
 65                  70                  75                  80

Asn Met Asn Leu Arg Thr Leu Ser Glu Lys Ala Arg Asp Asp Met Lys
                 85                  90                  95

Asn Ser Pro Glu Asp Pro Glu Ala Thr Met Thr Asp Gln Gly Pro Ser
            100                 105                 110

Lys Glu Lys Val Pro Glu Asn Lys Tyr Gly Met Thr Lys Leu Ile Leu
        115                 120                 125

Gly Val Ser Asp Ile Ser Asp Ser Asn Asn Lys His Lys Tyr Val Gly
    130                 135                 140

Ile His Ser Ser Phe Ala Glu Ile Ser Gln Ala Met Glu Gln Glu Gly
145                 150                 155                 160

Ala Thr Ala Ala Glu Thr Glu Glu Gln Gly His Gly Gly Asp Thr Trp
                165                 170                 175

Asp Tyr Lys Ser His Val Met Thr Lys Phe Ala Glu Glu Asp Val
            180                 185                 190

Arg Arg Ser Phe Glu Asn Thr Ala Ala Asp Trp Pro Glu Met Gln Thr
        195                 200                 205

Leu Ala Gly Ala Phe Asp Ser Asp Arg Trp Gly Phe Arg Pro Arg Thr
    210                 215                 220

Val Val Leu His Gly Lys Ser Gly Ile Gly Lys Ser Ala Leu Ala Arg
225                 230                 235                 240

Arg Ile Val Leu Cys Trp Ala Gln Gly Leu Tyr Gln Gly Met Phe
                245                 250                 255

Ser Tyr Val Phe Phe Leu Pro Val Arg Glu Met Gln Arg Lys Lys Glu
            260                 265                 270
```

```
Ser Ser Val Thr Glu Phe Ile Ser Arg Glu Trp Pro Asp Ser Gln Ala
        275                 280                 285

Pro Val Thr Glu Ile Met Ser Arg Pro Glu Arg Leu Leu Phe Ile Ile
        290                 295                 300

Asp Gly Phe Asp Leu Gly Ser Val Leu Asn Asn Asp Thr Lys Leu
305                 310                 315                 320

Cys Lys Asp Trp Ala Glu Lys Gln Pro Pro Phe Thr Leu Ile Arg Ser
                325                 330                 335

Leu Leu Arg Lys Val Leu Pro Glu Ser Phe Leu Ile Val Thr Val
            340                 345                 350

Arg Asp Val Gly Thr Glu Lys Leu Lys Ser Glu Val Ser Pro Arg
                355                 360                 365

Tyr Leu Leu Val Arg Gly Ile Ser Gly Glu Gln Arg Ile His Leu Leu
370                 375                 380

Leu Glu Arg Gly Ile Gly Glu His Gln Lys Thr Gln Gly Leu Arg Ala
385                 390                 395                 400

Ile Met Asn Asn Arg Glu Leu Leu Asp Gln Cys Gln Val Pro Ala Val
                405                 410                 415

Gly Ser Leu Ile Cys Val Ala Leu Gln Leu Gln Asp Val Val Gly Glu
            420                 425                 430

Ser Val Ala Pro Phe Asn Gln Thr Leu Thr Gly Leu His Ala Ala Phe
        435                 440                 445

Val Phe His Gln Leu Thr Pro Arg Gly Val Val Arg Arg Cys Leu Asn
        450                 455                 460

Leu Glu Glu Arg Val Val Leu Lys Arg Phe Cys Arg Met Ala Val Glu
465                 470                 475                 480

Gly Val Trp Asn Arg Lys Ser Val Phe Asp Gly Asp Leu Met Val
                485                 490                 495

Gln Gly Leu Gly Glu Ser Glu Leu Arg Ala Leu Phe His Met Asn Ile
            500                 505                 510

Leu Leu Pro Asp Ser His Cys Glu Glu Tyr Tyr Thr Phe Phe His Leu
        515                 520                 525

Ser Leu Gln Asp Phe Cys Ala Ala Leu Tyr Tyr Val Leu Glu Gly Leu
        530                 535                 540

Glu Ile Glu Pro Ala Leu Cys Pro Leu Tyr Val Glu Lys Thr Lys Arg
545                 550                 555                 560

Ser Met Glu Leu Lys Gln Ala Gly Phe His Ile His Ser Leu Trp Met
                565                 570                 575

Lys Arg Phe Leu Phe Gly Leu Val Ser Glu Asp Val Arg Arg Pro Leu
            580                 585                 590

Glu Val Leu Leu Gly Cys Pro Val Pro Leu Gly Val Lys Gln Lys Leu
        595                 600                 605

Leu His Trp Val Ser Leu Leu Gly Gln Gln Pro Asn Ala Thr Thr Pro
        610                 615                 620

Gly Asp Thr Leu Asp Ala Phe His Cys Leu Phe Glu Thr Gln Asp Lys
625                 630                 635                 640

Glu Phe Val Arg Leu Ala Leu Asn Ser Phe Gln Glu Val Trp Leu Pro
                645                 650                 655

Ile Asn Gln Asn Leu Asp Leu Ile Ala Ser Ser Phe Cys Leu Gln His
            660                 665                 670

Cys Pro Tyr Leu Arg Lys Ile Arg Val Asp Val Lys Gly Ile Phe Pro
        675                 680                 685

Arg Asp Glu Ser Ala Glu Ala Cys Pro Val Val Pro Leu Trp Met Arg
```

-continued

```
                690                 695                 700
Asp Lys Thr Leu Ile Glu Glu Gln Trp Glu Asp Phe Cys Ser Met Leu
705                 710                                     720

Gly Thr His Pro His Leu Arg Gln Leu Asp Leu Gly Ser Ser Ile Leu
                725                 730                 735

Thr Glu Arg Ala Met Lys Thr Leu Cys Ala Lys Leu Arg His Pro Thr
            740                 745                 750

Cys Lys Ile Gln Thr Leu Met Phe Arg Asn Ala Gln Ile Thr Pro Gly
            755                 760                 765

Val Gln His Leu Trp Arg Ile Val Met Ala Asn Arg Asn Leu Arg Ser
770                 775                 780

Leu Asn Leu Gly Gly Thr His Leu Lys Glu Glu Asp Val Arg Met Ala
785                 790                 795                 800

Cys Glu Ala Leu Lys His Pro Lys Cys Leu Leu Glu Ser Leu Arg Leu
            805                 810                 815

Asp Cys Cys Gly Leu Thr His Ala Cys Tyr Leu Lys Ile Ser Gln Ile
            820                 825                 830

Leu Thr Thr Ser Pro Ser Leu Lys Ser Leu Ser Leu Ala Gly Asn Lys
    835                 840                 845

Val Thr Asp Gln Gly Val Met Pro Leu Ser Asp Ala Leu Arg Val Ser
850                 855                 860

Gln Cys Ala Leu Gln Lys Leu Ile Leu Glu Asp Cys Gly Ile Thr Ala
865                 870                 875                 880

Thr Gly Cys Gln Ser Leu Ala Ser Ala Leu Val Ser Asn Arg Ser Leu
                885                 890                 895

Thr His Leu Cys Leu Ser Asn Asn Ser Leu Gly Asn Glu Gly Val Asn
                900                 905                 910

Leu Leu Cys Arg Ser Met Arg Leu Pro His Cys Ser Leu Gln Arg Leu
        915                 920                 925

Met Leu Asn Gln Cys His Leu Asp Thr Ala Gly Cys Gly Phe Leu Ala
        930                 935                 940

Leu Ala Leu Met Gly Asn Ser Trp Leu Thr His Leu Ser Leu Ser Met
945                 950                 955                 960

Asn Pro Val Glu Asp Asn Gly Val Lys Leu Leu Cys Glu Val Met Arg
                965                 970                 975

Glu Pro Ser Cys His Leu Gln Asp Leu Glu Leu Val Lys Cys His Leu
            980                 985                 990

Thr Ala Ala Cys Cys Glu Ser Leu Ser Cys Val Ile Ser Arg Ser Arg
            995                 1000                1005

His Leu Lys Ser Leu Asp Leu Thr Asp Asn Ala Leu Gly Asp Gly Gly
    1010                1015                1020

Val Ala Ala Leu Cys Glu Gly Leu Lys Gln Lys Asn Ser Val Leu Thr
1025                1030                1035                1040

Arg Leu Gly Leu Lys Ala Cys Gly Leu Thr Ser Asp Cys Cys Glu Ala
                1045                1050                1055

Leu Ser Leu Ala Leu Ser Cys Asn Arg His Leu Thr Ser Leu Asn Leu
            1060                1065                1070

Val Gln Asn Asn Phe Ser Pro Lys Gly Met Met Lys Leu Cys Ser Ala
    1075                1080                1085

Phe Ala Cys Pro Thr Ser Asn Leu Gln Ile Ile Gly Leu Trp Lys Trp
    1090                1095                1100

Gln Tyr Pro Val Gln Ile Arg Lys Leu Leu Glu Glu Val Gln Leu Leu
1105                1110                1115                1120
```

```
Lys Pro Arg Val Val Ile Asp Gly Ser Trp His Ser Phe Asp Glu Asp
            1125                1130                1135

Asp Arg Tyr Trp Trp Lys Asn
            1140

<210> SEQ ID NO 5
<211> LENGTH: 1111
<212> TYPE: PRT
<213> ORGANISM: Mus sp.

<400> SEQUENCE: 5

Met Gly Pro Pro Glu Lys Glu Ser Lys Ala Ile Leu Lys Ala Arg Gly
  1               5                  10                  15

Leu Glu Glu Glu Gln Lys Ser Glu Arg Lys Met Thr Ser Pro Glu Asn
             20                  25                  30

Asp Ser Lys Ser Ile Gln Lys Asp Gln Gly Pro Glu Gln Glu Gln Thr
         35                  40                  45

Ser Glu Ser Thr Met Gly Pro Pro Glu Lys Asp Ser Lys Ala Ile Leu
     50                  55                  60

Lys Ala Arg Gly Leu Glu Glu Glu Gln Lys Ser Glu Ser Thr Met Ser
 65                  70                  75                  80

Pro Ser Glu Asn Val Ser Arg Ala Ile Leu Lys Asp Ser Gly Ser Glu
                 85                  90                  95

Glu Val Glu Gln Ala Ser Glu Arg Lys Met Thr Ser Pro Glu Asn Asp
            100                 105                 110

Ser Lys Ser Ile Gln Lys Asp Gln Gly Pro Glu Gln Glu Gln Thr Ser
        115                 120                 125

Glu Thr Leu Gln Ser Lys Glu Glu Asp Glu Val Thr Glu Ala Asp Lys
    130                 135                 140

Asp Asn Gly Gly Asp Leu Gln Asp Tyr Lys Ala His Val Ile Ala Lys
145                 150                 155                 160

Phe Asp Thr Ser Val Asp Leu His Tyr Asp Ser Pro Glu Met Lys Leu
                165                 170                 175

Leu Ser Asp Ala Phe Lys Pro Tyr Gln Lys Thr Phe Gln Pro His Thr
            180                 185                 190

Ile Ile Leu His Gly Arg Pro Gly Val Gly Lys Ser Ala Leu Ala Arg
        195                 200                 205

Ser Ile Val Leu Gly Trp Ala Gln Gly Lys Leu Phe Gln Lys Met Ser
    210                 215                 220

Phe Val Ile Phe Phe Ser Val Arg Glu Ile Lys Trp Thr Glu Lys Ser
225                 230                 235                 240

Ser Leu Ala Gln Leu Ile Ala Lys Glu Cys Pro Asp Ser Trp Asp Leu
                245                 250                 255

Val Thr Lys Ile Met Ser Gln Pro Glu Arg Leu Leu Phe Val Ile Asp
            260                 265                 270

Gly Leu Asp Asp Met Asp Ser Val Leu Gln His Asp Met Thr Leu
        275                 280                 285

Ser Arg Asp Trp Lys Asp Glu Gln Pro Ile Tyr Ile Leu Met Tyr Ser
    290                 295                 300

Leu Leu Arg Lys Ala Leu Leu Pro Gln Ser Phe Leu Ile Ile Thr Thr
305                 310                 315                 320

Arg Asn Thr Gly Leu Glu Lys Leu Lys Ser Met Val Val Ser Pro Leu
                325                 330                 335

Tyr Ile Leu Val Glu Gly Leu Ser Ala Ser Arg Arg Ser Gln Leu Val
```

-continued

```
                340                 345                 350
Leu Glu Asn Ile Ser Asn Glu Ser Asp Arg Ile Gln Val Phe His Ser
                355                 360                 365
Leu Ile Glu Asn His Gln Leu Phe Asp Gln Cys Gln Ala Pro Ser Val
            370                 375                 380
Cys Ser Leu Val Cys Glu Ala Leu Gln Leu Gln Lys Lys Leu Gly Lys
385                 390                 395                 400
Arg Cys Thr Leu Pro Cys Gln Thr Leu Thr Gly Leu Tyr Ala Thr Leu
                405                 410                 415
Val Phe His Gln Leu Thr Leu Lys Arg Pro Ser Gln Ser Ala Leu Ser
            420                 425                 430
Gln Glu Glu Gln Ile Thr Leu Val Gly Leu Cys Met Met Ala Ala Glu
        435                 440                 445
Gly Val Trp Thr Met Arg Ser Val Phe Tyr Asp Asp Leu Lys Asn
    450                 455                 460
Tyr Ser Leu Lys Glu Ser Glu Ile Leu Ala Leu Phe His Met Asn Ile
465                 470                 475                 480
Leu Leu Gln Val Gly His Asn Ser Glu Gln Cys Tyr Val Phe Ser His
            485                 490                 495
Leu Ser Leu Gln Asp Phe Phe Ala Ala Leu Tyr Tyr Val Leu Glu Gly
            500                 505                 510
Leu Glu Glu Trp Asn Gln His Phe Cys Phe Ile Glu Asn Gln Arg Ser
        515                 520                 525
Ile Met Glu Val Lys Arg Thr Asp Asp Thr Arg Leu Leu Gly Met Lys
    530                 535                 540
Arg Phe Leu Phe Gly Leu Met Asn Lys Asp Ile Leu Lys Thr Leu Glu
545                 550                 555                 560
Val Leu Phe Glu Tyr Pro Val Ile Pro Thr Val Glu Gln Lys Leu Gln
                565                 570                 575
His Trp Val Ser Leu Ile Ala Gln Gln Val Asn Gly Thr Ser Pro Met
            580                 585                 590
Asp Thr Leu Asp Ala Phe Tyr Cys Leu Phe Glu Ser Gln Asp Glu Glu
            595                 600                 605
Phe Val Gly Gly Ala Leu Lys Arg Phe Gln Glu Val Trp Leu Leu Ile
        610                 615                 620
Asn Gln Lys Met Asp Leu Lys Val Ser Ser Tyr Cys Leu Lys His Cys
625                 630                 635                 640
Gln Asn Leu Lys Ala Ile Arg Val Asp Ile Arg Asp Leu Leu Ser Val
                645                 650                 655
Asp Asn Thr Leu Glu Leu Cys Pro Val Val Thr Val Gln Glu Thr Gln
            660                 665                 670
Cys Lys Pro Leu Leu Met Glu Trp Trp Gly Asn Phe Cys Ser Val Leu
        675                 680                 685
Gly Ser Leu Arg Asn Leu Lys Glu Leu Asp Leu Gly Asp Ser Ile Leu
    690                 695                 700
Ser Gln Arg Ala Met Lys Ile Leu Cys Leu Glu Leu Arg Asn Gln Ser
705                 710                 715                 720
Cys Arg Ile Gln Lys Leu Thr Phe Lys Ser Ala Glu Val Val Ser Gly
                725                 730                 735
Leu Lys His Leu Trp Lys Leu Phe Ser Asn Gln Asn Leu Lys Tyr
            740                 745                 750
Leu Asn Leu Gly Asn Thr Pro Met Lys Asp Asp Met Lys Leu Ala
        755                 760                 765
```

```
Cys Glu Ala Leu Lys His Pro Lys Cys Ser Val Glu Thr Leu Arg Leu
770                 775                 780

Asp Ser Cys Glu Leu Thr Ile Ile Gly Tyr Glu Met Ile Ser Thr Leu
785                 790                 795                 800

Leu Ile Ser Thr Thr Arg Leu Lys Cys Leu Ser Leu Ala Lys Asn Arg
                805                 810                 815

Val Gly Val Lys Ser Met Ile Ser Leu Gly Asn Ala Leu Ser Ser Ser
            820                 825                 830

Met Cys Leu Leu Gln Lys Leu Ile Leu Asp Asn Cys Gly Leu Thr Pro
        835                 840                 845

Ala Ser Cys His Leu Leu Val Ser Ala Leu Phe Ser Asn Gln Asn Leu
    850                 855                 860

Thr His Leu Cys Leu Ser Asn Asn Ser Leu Gly Thr Glu Gly Val Gln
865                 870                 875                 880

Gln Leu Cys Gln Phe Leu Arg Asn Pro Glu Cys Ala Leu Gln Arg Leu
                885                 890                 895

Ile Leu Asn His Cys Asn Ile Val Asp Asp Ala Tyr Gly Phe Leu Ala
            900                 905                 910

Met Arg Leu Ala Asn Asn Thr Lys Leu Thr His Leu Ser Leu Thr Met
        915                 920                 925

Asn Pro Val Gly Asp Gly Ala Met Lys Leu Leu Cys Glu Ala Leu Lys
    930                 935                 940

Glu Pro Thr Cys Tyr Leu Gln Glu Leu Glu Leu Val Asp Cys Gln Leu
945                 950                 955                 960

Thr Gln Asn Cys Cys Glu Asp Leu Ala Cys Met Ile Thr Thr Thr Lys
                965                 970                 975

His Leu Lys Ser Leu Asp Leu Gly Asn Asn Ala Leu Gly Asp Lys Gly
            980                 985                 990

Val Ile Thr Leu Cys Glu Gly Leu Lys Gln Ser Ser Ser Ser Leu Arg
        995                 1000                1005

Arg Leu Gly Leu Gly Ala Cys Lys Leu Thr Ser Asn Cys Cys Glu Ala
    1010                1015                1020

Leu Ser Leu Ala Ile Ser Cys Asn Pro His Leu Asn Ser Leu Asn Leu
1025                1030                1035                1040

Val Lys Asn Asp Phe Ser Thr Ser Gly Met Leu Lys Leu Cys Ser Ala
                1045                1050                1055

Phe Gln Cys Pro Val Ser Asn Leu Gly Ile Gly Leu Trp Lys Gln
            1060                1065                1070

Glu Tyr Tyr Ala Arg Val Arg Arg Gln Leu Glu Glu Val Glu Phe Val
        1075                1080                1085

Lys Pro His Val Val Ile Asp Gly Asp Trp Tyr Ala Ser Asp Glu Asp
    1090                1095                1100

Asp Arg Asn Trp Trp Lys Asn
1105                1110

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
atggaaggag acaaatcgct c                                          21
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
tagttggcat tcttttgatg                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
cacatgaaca tccttctccc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
cacagtcctc cagtatcagc                                                    20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
cctcccaagt tgagggatct t                                                  21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
tacccctggt gtgcagcac                                                     19

HUMAN MATER PROTEINS

The invention relates to Mater and its use as a pharmaceutical agent for influencing apoptotic processes that play a basic role in birth control.

For birth control, the "standard pill" is the most frequently used means of choice as a female contraceptive agent. Its regular intake results in ovulation inhibition in women. The principle of this method is that by taking the pill, suppression of the endogenic steroid hormone production in the ovary and thus ovulation inhibition result. A drawback is that a natural cycle thus is no longer present in women. Moreover, in connection with taking the pill in patients who are potentially at risk, side effects such as, for example, tightness of the chest, weight increase, etc., can occur.

Numerous studies confirm that fertility decreases in women as they grow older. This can be attributed to, i.a., a deteriorating quality of ovocytes, an elevated abortion rate, and increased exposure to infectious germs (e.g., chlamydia or gonococci). Since, in industrial countries, however, the age of women who are pregnant for the first time is always moving further back, it is necessary to find possibilities for improving fertility. This is true for women and also for men. For couples with fertility disorders, techniques of assisted reproduction are now available (in vitro fertilization (IVF); gamete intrafallopian transfer (GIFT), intrauterine insemination). These methods are invasive, however, and are connected in most cases with a prior follicle maturation stimulation in women by proteohormones (follicle-stimulating hormone/FSH). This can result in unpleasant side effects such as headaches or pains in the abdomen, but also in the worst case in the so-called ovarian hyperstimulation syndrome.

There therefore exists the urgent need to provide new substances and agents for birth control, i.e., both to promote fertility and to inhibit fertility.

In mice, it was shown that female mice without an OP (ooplasm-specific protein)-1 gene are infertile (Tong and Nelson, 1999, Endocrinology 140, 3720–3726 and Tong et al., Nature Genetics, 2000, 26, 267–267), while the fertility of male animals remains unchanged. It was possible to show that the infertility is the result of a blocking of the development of the fertilized ovocyte after the two-cell stage. The cycle of the mouse is normal; animals ovulate spontaneously after stimulation with gonadotropin. Fertilized cells of these transgenic animals remain, however, in the two-cell stage without further development or degenerate about 3 days after fertilization. The OP-1 is also referred to as MATER (maternal-antigen-that-embryos-require).

In a mouse model of the autoimmune oophoritis, antibodies against mouse-MATER protein could be detected. This model has many similarities to the human clinical picture of "autoimmune-premature ovarian-failure," so that the possibility exists that a putative human MATER protein plays an important role in the regulation of fertility similar to the mouse-MATER. It is not known to date, however, whether a human homolog to the mouse-MATER protein exists.

In this invention, it was possible to show that human MATER is strongly expressed in the uterus. In this case, the expression in the inner layer of the uterus, the endometrium, shows a clear regulation based on the female cycle. The expression of Mater is significantly reduced in the so-called implantation window of the cycle (about 8 days after the increase of luteinizing hormone LH, which triggers ovulation) in comparison to the phase directly after the ovulation (see FIG. 4). By means of quantitative determinations, the mRNAs from the human endometrium of three different clinical study groups were compared with one another. The result of this study indicated that the mRNA of MATER in comparison to the control group (before opening the implantation window) is greatly reduced in group LH +8 (time of the open implantation window) in healthy women. In group LH +8/EMT (endometriosis patients), an increased amount of MATER-mRNA could be detected in 2 out of 3 patients. A cause of infertility, as it is observed in the case of endometriosis patients, can be based on the elevated MATER expression, since in the implantation window, thus at the time of the fertile phase, the MATER expression in the endometrium of fertile women is reduced.

A human MATER protein therefore represents a suitable target substance to identify new agents for birth control.

This invention represents a nucleic acid that already comprises a. the nucleotide sequence that is shown in Seq ID NO 1 or Seq ID NO 3, b. a nucleotide sequence that corresponds to a sequence from a, in the scope of the degeneration of the genetic code, or c. a nucleotide sequence that hybridizes with the sequences from a, or b, under stringent conditions with the function of a human MATER protein.

The term "hybridization under stringent conditions" according to this invention is defined by Sambrook et al. (Molecular Cloning, A Laboratory Manual, Cold Spring Harbor Laboratory Press, 1989). A stringent hybridization exists, for example, if after washing for 1 hour with 1×SSC and 0.1% SDS at 50° C., preferably at 55° C., especially preferably at 62° C. and most preferably at 68° C., especially for 1 hour in 0.2×SSC and 0.1% SDS at 55° C., preferably at 62° C. and most preferably at 68° C., a hybridization signal is still observed. The nucleic acids that hybridize under these conditions with the nucleic acid that is shown in Seq. ID NO 1 and/or 3 or a nucleotide sequence that corresponds to this sequence within the scope of the degeneration of the genetic code are also the subject matter of this invention.

Nucleic acids can produce single- or double-strand DNA, e.g., cDNA, or RNA, e.g., mRNA, cRNA, or pre-mRNA.

The nucleic acids that are shown in Seq ID NO 1 and Seq ID NO 3 code for a human MATER protein. They represent splice variants of the same gene. In the sequence that is shown in Seq ID NO 3, exon 4 is missing.

Preferred is the nucleic acid that comprises a protein-coding section of the nucleic acid sequence that is shown in Seq ID NO 1 or Seq ID NO 3. A protein-coding section of the sequence that is shown in Seq ID NO 1 is in the nucleotide range of 1 to 3489, and the sequence that is shown in Seq ID NO 3 is in the nucleotide range of 1 to 3432.

A subject of the invention is also a nucleic acid that codes for a polypeptide with the amino acid sequence that is shown in Seq ID NO 2 or Seq ID NO 4.

The nucleic acid according to the invention can be obtained from mammals, e.g., human cells, or from a cDNA library or a genomic library, which is obtained from, e.g., human cells. It can be isolated according to known techniques with use of short sections of the nucleic acid sequences that are shown in Seq ID NO 1 or Seq ID NO 3 as hybridization probes or amplification primers.

In addition, the invention relates to polypeptides that are coded by a nucleic acid according to the invention. These polypeptides have the function of a human MATER protein. The function of the MATER protein is that of an NTPase, which is connected with apoptosis. Malfunctions in the MATER protein result in an arrest of the development of the fertilized ovocytes that are found in the two-cell stage. The cells undergo apoptosis, and further development is no longer possible.

In addition, a subject of the invention is a polypeptide that comprises the amino acid sequence that is shown in Seq ID NO 2 or Seq ID NO 4.

The polypeptide according to the invention can be a recombinant polypeptide, a natural, isolated polypeptide or a synthetic polypeptide.

The polypeptide according to the invention contains various domains: a Dapin (Domain in apoptosis and interferon response) domain, a NACHT (NAIP, CIIA, HET- and TP-1) domain, and a DUF (Domain of unknown function) domain. These domains are linked with apoptosis (Staub, E. et al., TIBS, 2001, 26 (2), 83–85, Koonin, E. V., Aravind, L., TIBS, 2000, 25 (5), 223–224). This suggests that members of the NACHT family contain NTPases that have anti-apoptotic action. The Dapin domains, which are responsible for the formation of homodimers or heterodimers, were previously described in the case of proteins that are involved in apoptosis or inflammatory processes. MATER has an antiapoptotic action, while in the case of errors or malfunctions of the MATER protein, the cells go into apoptosis and a further development of the two-cell stage is no longer possible. In addition, MATER 14 contains so-called "leucin-rich repeats" (LRR, Kajava, A. V., 1998, J. Mol. Biol. 227, 519–527), which are responsible for the protein-protein interactions. Although the homology between the human sequence and the mouse sequence is only 52%, mouse-Mater polypeptide and human Mater polypeptide show a high sequence homology in the areas of all domains with the exception of the Dapin domain (see FIGS. 1 and 2).

The mRNA of the polypeptide according to the invention according to claim Seq ID NO 2 or Seq ID NO 4 is transcribed primarily in the ovaries, in the testes and in the placentas.

The polypeptide according to the invention or partial areas thereof (peptides) can be used for the production of antibodies. For the production of polyclonal antibodies, the polypeptides or peptides can be bonded to, e.g., KLH (Keyhole Limpet Hemocyanin), and animals, e.g., rabbits, can be sprayed. They can also be used for the production of monoclonal antibodies. For antibody production, a polypeptide or peptide according to the invention or a mixture of several peptides according to the invention can be used. In this case, the production of the antibodies is carried out according to standard processes, as they are described in, e.g., Kohler, G. and Milstein, C., Nature 1975, 256, 495–497 and Nelson, P. N. et al., Mol. Pathol. 2000, 53, 111–117.

Subjects of the invention are also the antibodies that are directed against a polypeptide according to the invention.

The antibodies according to the invention can be used for the detection of the polypeptides according to the invention. This can be carried out by, e.g., immunohistochemistry. The antibodies according to the invention can also be used in other immune tests, such as, e.g., an ELISA (enzyme linked immunosorbent assay) or in a radioimmuno test. Thus, the concentration of polypeptides according to the invention can be detected in tissue or cell extracts.

The detection of the expression of the polypeptide according to the invention can also be carried out via the detection of mRNA in the cells. The subject of the invention is therefore also the use of a probe with nucleic acid sequences that are complementary to the nucleic acid sequences that code for the peptides according to the invention for the production of a reagent for the detection of the presence of mRNA in cells according to the invention. A probe is a short strand of DNA with at least 14 nucleotides. The probes according to the invention can be used in, e.g., a Northern Blot analysis. This method is described in, e.g., Sambrook, J. et al., 1989, Cold Spring Harbor Laboratory Press. Other methods for detecting RNA are in-situ hybridization, RNAse protection assay or PCR.

In addition, the invention relates to antisense molecules that are directed against the nucleic acid sequence according to the invention and can suppress the expression of the MATER protein. Such molecules can be used specifically for contraception.

In addition, subjects of the invention are vectors that contain at least one copy of the nucleic acid according to the invention. Vectors can be prokaryotic or eukaryotic vectors. Examples of vectors are pPRO (Clontech), pBAD (Invitrogen), pSG5 (Stratagene), pC1 (Promega), pIRES (Clontech), pBAC (Clontech), pMET (Invitrogen), and pBlueBac (Invitrogen). The nucleic acids according to the invention can be inserted into these vectors with the methods that are known to one skilled in the art. In connection with expression signals, such as, e.g., promoters and enhancers, the nucleic acids according to the invention are preferably found in the vector.

The invention also relates to cells that are transfixed with a nucleic acid sequence according to the invention or with a vector according to the invention. As cells, e.g., *E. coli,* yeast, Pichia, Sf9, COS, CV-1 or BHK can be used. These cells can be used both for the production of the polypeptide according to the invention or for test systems.

In the USA, 1% of women suffer from "autoimmune premature ovarian failure," a disease whose clinical syndrome is characterized by the formation of amenorrhea (less than 40 years), by infertility and by menopausal symptoms, caused by hypoestrogenemia and hypergonadotropinemia (Nelson and Tong, Endocrinology, 1999, 140, 3720–3726). In an analogous mouse model of the autoimmune-oophoritis, it was possible to show that one of the causes of this disease is the formation of antibodies against the mouse-Mater protein. A subject of the invention is therefore the use of the polypeptides according to the invention or the nucleic acids that code for this as a target substance for the production of an agent for treating fertility disorders, whose cause lies in a malfunction of the MATER protein.

In particular, the invention includes the use of
a. A nucleic acid according to the invention,
b. A polypeptide according to the invention, or
c. A cell according to the invention for identifying effectors of a polypeptide according to the invention. Effectors are substances that have an inhibitory or activating effect on the polypeptide according to the invention and that are able to influence the MATER function of the polypeptides according to the invention.

For the specific contraception, it may be advantageous to maintain the embryos in the two-cell stage to prevent further development. By administering antibodies that are directed against the polypeptide according to the invention, the endogenic function of MATER can be impaired and/or eliminated. The invention therefore also relates to the use of antibodies that are directed against a polypeptide according to the invention.

In addition, the invention relates to a test system for identifying effectors of a polypeptide according to the invention, whereby a polypeptide according to the invention can be incubated as a complete or partial sequence thereof with a modulator and, for example, the interaction of MATER with proteins or partial sequences of other proteins can be measured (protein interaction assay). The protein-protein interactions are to be measured in the mammalian two-hybrid assay system (stratagenes), in which the interaction between MATER and other proteins or partial sequences thereof is determined via the activation of the expression of a reporter gene.

In addition, the invention relates to a test system for identifying effectors of a polypeptide according to the invention, whereby a polypeptide according to the invention can be incubated as a complete or partial sequence thereof with a modulator, and, for example, the amount of hydrolyzed nucleotide can be measured. As a partial sequence, e.g., the area that comprises the "leucine-rich repeats" and the NACHT domains or shorter strands thereof can be used. The activity of the effectors can be measured, e.g., by labeled NTP being used and the cleavage in NDP and Pi being measured (NTPase assay).

In addition to the hydrolysis of NTP, a binding test can also be performed to identify substances that prevent the binding of NTP to MATER.

This binding test can also be performed with a cell according to the invention that contains the polypeptide according to the invention. In addition to the binding of the substances to be tested on MATER, an intracellular effect can also be measured.

The effectors of the polypeptide according to the invention can be used to treat diseases that are based on malfunctions in the MATER protein. Examples of this are ovarian dysfunction, "autoimmune premature ovarian failure," inflammatory diseases and diseases of the immune system. In addition, these effectors can be used to treat female infertility.

The effectors of the polypeptide according to the invention can also be used for contraception in women. If they block the NTPase activity of Mater, the fertilized ovocyte undergoes apoptosis, and further development is no longer possible.

In addition, the invention relates to a test system for identifying effectors of a polypeptide according to the invention, whereby a polypeptide according to the invention can be incubated as a complete or partial sequence thereof with a modulator, and for example, apoptosis induction in the cells can be measured. As a partial sequence, e.g., the area that comprises the "leucin-rich repeats" and the NACHT domains or shorter strands thereof can be used. The activity of the effectors can be measured, e.g., by their influence on the apoptosis induction in cells that were incubated with Mater or a fragment of Mater (cell-death assay).

It was found that the polypeptide according to the invention produces an antigen that is absolutely necessary for the development of the embryo over the two-cell stage. The antigen could be administered directly to women who suffer from fertility disorders. Another possibility was the use of antigen in vitro to an oocyte culture. A further possibility was the addition of the antigen to the fertilizing medium or to the medium for the culture of the embryo. The thus prepared oocytes are then used for in-vitro fertilization. A treatment with antibodies against the polypeptide according to the invention or segments therefore could be used by women for birth control.

In addition, the invention relates to a process for the preparation of a pharmaceutical agent, whereby a. Substances are brought into contact with a test system according to the invention,
b. The action of the substances on the test system in comparison to controls is measured,
c. A substance that in step b. shows a modulation of the activity of the polypeptides according to the invention is identified,
d. And the substance that is identified in step c. is mixed with the formulation substances that are commonly used in pharmaceutics.

The activity of the polypeptide according to the invention is defined as the NTPase activity of the polypeptide or its property to induce apoptosis. A substance that is identified by a process according to the invention can optionally be optimized relative to metabolic stability, activity in a test system according to the invention and/or bio-availability. To this end, methods that are common in chemistry can be used.

The preferred preparations consist in a form of dispensing that is suitable for oral, enteral or parenteral administration. Such forms for dispensing are, for example, tablets, film tablets, coated tablets, pills, capsules, powder or depot forms as well as suppositories. Corresponding tablets can be obtained, for example, by mixing active ingredient with known adjuvants, for example inert diluents such as dextrose, sugar, sorbitol, mannitol, polyvinyl pyrrolidone, explosives such as corn starch or alginic acid, binders such as starch or gelatin, lubricants such as carboxypolymethylene, carboxymethyl cellulose, cellulose acetate phthalate or polyvinyl acetate. The tablets can also consist of several layers.

The invention also relates to a process for determining the autoimmune antibodies against the MATER protein. Autoimmunity is a well-described mechanism for "premature ovarian failure," a disease in which the ovaries of women are attacked by their own immune systems; an inflammation of the ovaries is the result in most cases. For the diagnosis of fertility disorders, bodily samples (tissue or liquids) in women can be studied. The content of autoimmune antibodies can be determined by means of an immune test, such as, e.g., an ELISA (enzyme linked immunosorbent assay) test or in a radioimmuno test. The presence of autoimmune antibodies in tissue or cell extracts thus can be detected and allows conclusions on the state of health of the ovary.

It has also been found that the ovocyte quality depends on the Mater expression. The Mater expression in ovocytes therefore can also be used as a diagnostic marker for determining the ovocyte quality.

In addition, the invention relates to a process for the diagnosis of diseases, whose causes include mutations of the MATER protein. For this purpose, DNA chips can be used. The invention therefore relates in addition to a DNA chip, in which at least one oligonucleotide is immobilized, which corresponds to the complete cDNA sequence or a partial sequence or a complementary sequence to the one described in Seq ID 1. The invention thus also relates to the use of a DNA chip according to the invention for diagnosis of fertility disorders in, i.a., the ovary and endometrium.

DNA chips, also known as DNA microarrays, are miniaturized vehicles, in most cases made of glass or silicon, on whose surfaces DNA molecules of known sequence are immobilized in an ordered grid in high density. The surface-bonded DNA molecules are hybridized with complementary, optionally labeled nucleic acids. The labeling can be a fluorescence dye.

In the case of oligonucleotide chips, the oligonucleotides, which can be bonded to a DNA chip according to the invention, represent partial sequences of the gene products (mRNA or cDNA that is derived therefrom). One or more oligonucleotides per gene can be bonded to the DNA chip. Preferred are 25 nucleotide-long oligonucleotides. The latter are preferably selected from the respective 3'-untranslated end of the gene. Methods for production and use of DNA chips are described in, e.g., U.S. Pat. Nos. 5,578,832; 5,556,752 and 5,510,270.

In the case of cDNA chips, the complete gene products (cDNAs) or subfragments (200–500 bp long) are bonded to the chip. The method is described in, e.g., Eckmann, L. et al., J. Biol Chem., 2000, 275 (19), 14084–14094.

First, the suitable DNA sequences are determined according to Seq ID NO 1 or Seq ID NO 3. Sequences that can hybridize with the selected gene transcripts are suitable. The oligonucleotides are then produced on the chip by a chemical process that is based on the photolithographic process. For this purpose, photolithographic masks that were produced by suitable computer algorithms are used.

The labeled RNA is incubated with the chip in a hybridization furnace. Then, the chip is analyzed in a scanner that determines the hybridization profile. It can thus be determined whether changes to the transcript have occurred (e.g., mutations, truncations). It also makes possible the quantification of the transcript and thus the MATER protein and sheds light on, e.g., a mutation in the promoter.

It has been found that during the implantation window (LH +8), Mater is expressed to a smaller extent than in the prereceptive phase (LH +4). By determining the MATER expression, the optimal time for the implantation of oocytes, which were fertilized in vitro, can accordingly be determined. Moreover, the determination of the Mater expression can be used as a diagnostic marker for determining the implantation window in the endometrium.

DESCRIPTION OF THE FIGURES

FIG. 1 shows a multiple sequence alignment of the MATER proteins of mice (SEQ ID NO: 5) and humans (SEQ ID NO: 2).

FIG. 2 indicates the localization of the various domains within the human MATER protein. The "from" and "to" columns relate to the amino acid numbering according to Seq ID 2.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The molecular-biological methods that are used in the Examples, such as, e.g., polymerase chain reaction (PCR), production of cDNA, cloning of DNA, and sequencing of DNA, were performed as described in known textbooks, such as, for example, in Molecular Cloning, A Laboratory Manual (Sambrook, J. et al., 1989, Cold Spring Harbor Laboratory Press).

Example 1

Cloning, Expression and Purification of the Human Mater Protein

For the expression of the two splice variants of the Mater protein, the coding area was amplified by means of the polymerase chain reaction (for reaction conditions, see Example 2) (primer for the N-terminal area 5' ATGGAAG-GAGACAAATCGCTC 3' (SEQ ID NO: 6); primer for the C-terminal area: 5' TAGTTGGCATTCTTTTGATG 3') (SEQ ID NO: 7), and inserted in the baculovirus expression vector pBlueBac4.5/V5-His-TOPO (Invitrogen) or the eukaryotic expression vector pcDNA3.1/V5/His-TOPO (Invitrogen). To simplify detection and purification, a fusion with an His-tag was carried out. After co-transfection of insect cells with the Bac-N-Blue DNA, recombinant viruses that were identified by a PCR process were produced. A phage stock was then applied and used in larger amounts for additional transfections and production of Mater. The purification of the His-tagged proteins was carried out via a nickel affinity column.

Example 2

Figure 3A:
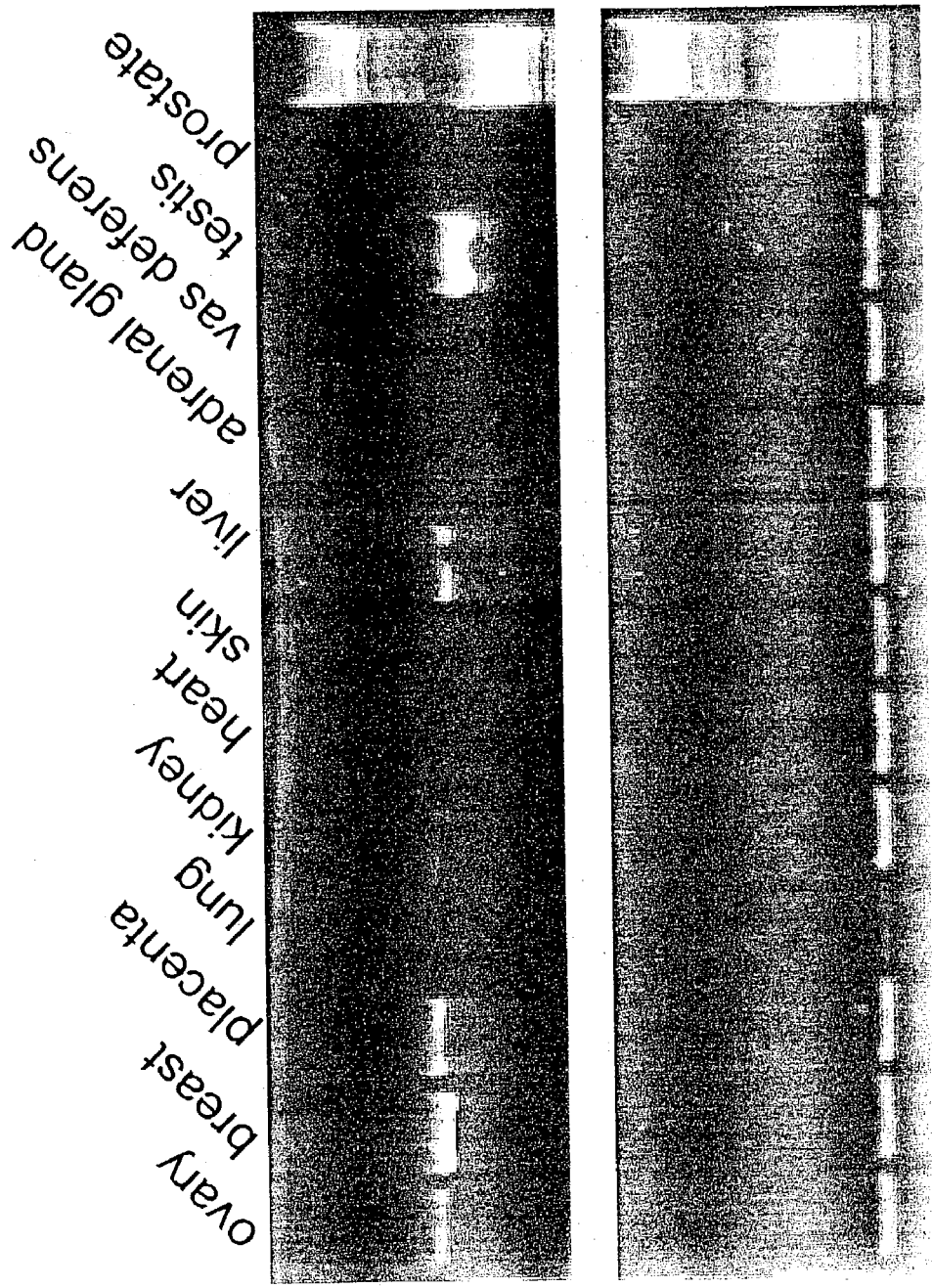
FIG. 3a shows the mRNA expression pattern of the human MATER protein in various tissues, demonstrated by the PCR. As an internal control, primers for cyclooxygenase (COX) were used. After the PCR amplification, the products were separated on an agarose gel and colored with ethidium bromide.
Figure 3B:
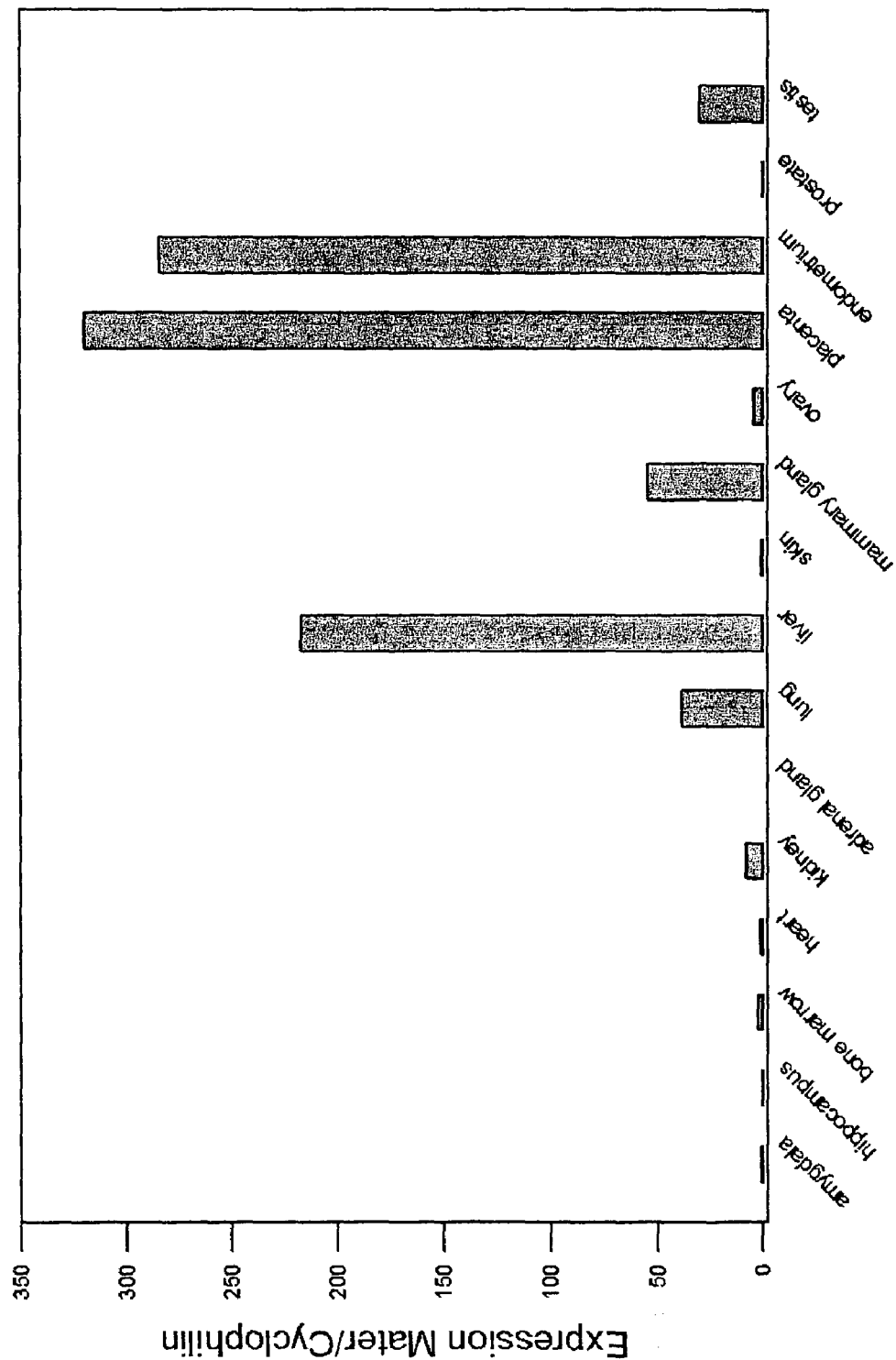
FIG. 3b shows the gene expression of RNA from MATER in various tissues, demonstrated by the real-time quantitative PCR method. It is readily evident that MATER is strongly expressed in the placenta and the endometrium. In the ovary, MATER is only weakly expressed. Here, these are ovaries from menopausal patients. In these ovaries, only very few ovocytes are present, and these ovocytes in addition are of lower quality, so that Mater is expressed only slightly.
Figure 4:
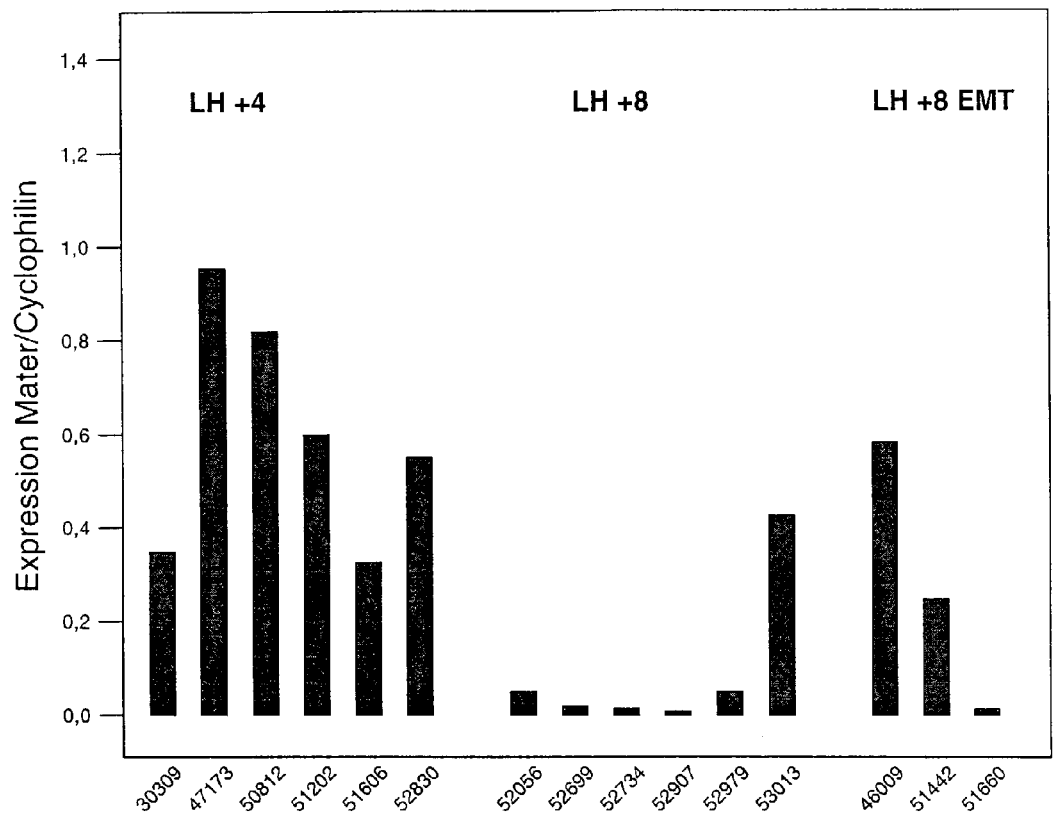
FIG. 4 shows the gene expression of the RNA from MATER in the endometrium, demonstrated by the real-time quantitative PCR method. A greatly reduced regulation of the human MATER gene in the group (LH +8) in comparison to the group LH +4 is clear. Specific "primers" for the MATER were used. Group LH +4: before the opening of the implantation window; group LH +8: time of the open implantation window in healthy women; group LH +8 EMT: time of the open implantation window in women who have the disease endometriosis; LH: luteinizing hormone; 4 or 8: period in days.

Studies Regarding the Expression of mRNA of the Human Mater Protein a) To study the expression of mRNA, a PCR was carried out as follows:

As templates, cDNA from the following tissues was used: bone, vas deferens, prostate, testis, placenta, breast, ovary, adrenal gland, skin, kidney and lung. The reaction batch contains: 2 µl of cDNA; 20 µm of primer (antisense primer: 5' cacatgaacatccttctccc 3' (SEQ ID NO: 8); sense primer: 5' cacagtcctccagtatcagc 3' (SEQ ID NO: 9)), 10 mmol of NTP; 1.5 mmol of $MgCl_2$ and 0.5 U of Taq gold (Perkin Elmer). The PCR conditions are 94° C. for 10 minutes, then 40 cycles at 94° C. for 1 minute; 58° C. for 1 minute; 72° C. for 1.5 minutes. Then, an aliquot was applied to a 1% agarose gel in 1 X TAE-running buffer. Under these conditions, an expression of the mRNA could be found in the following tissues: testis, placenta and ovary (see FIG. 3a).

b) Determination of the MATER-RNA amounts in endometrial samples by real-time quantitative RT-PCR analysis:

The endometrium was removed from patients who belong to the three groups LH +4, LH +8, and LH +8/endometriosis and shock-frozen in liquid nitrogen. Total-RNA was isolated from the tissues pulverized by "mortars" under liquid nitrogen by means of TRIZOL (Invitrogen). Starting from 5 μg of total-RNA, first DNase I-digestion (Invitrogen) and then a first-strand-synthesis were performed by using the SUPER-SCRIPT First-Strand Synthesis System for RT-PCR (Invitrogen). For the amplification of the transcripts for relative quantification, 0.125 μl of first-strand-DNA was used. With use of human Mater-specific primer pairs (forward primer: 5' CCT CCC AAG TTG AGG GAT CTT-3' (SEQ ID NO: 10) and reverse primer: 5' TAG CCC TGG TGT GCA GCA C-3' (SEQ ID NO: 11), the amplification was performed under the following PCR conditions: 10 minutes, 95° C.; 15 seconds, 95° C., 1 minute; 60° C. (40 cycles). As internal controls, primers were used for human cyclophilin (huCYC) Part Number 4310857 (PE Biosystems) in the PCR. The measurement of the fluorescence as a yardstick for the increase of amplification products was carried out online by means of an ABI Prism 7700 Sequence Detector (PE Biosystems). The purity of the amplification products was examined by plotting melt curves (see FIGS. 3b and 4).

Example 3

Test System for Finding Substances that Influence the NTPase Activity

A standard NTPase assay was performed as follows: Incubation for 30 minutes at 30° C. 5–30 pMol of the purified Mater protein or a fragment that encompasses the NTPase domain was incubated in a reaction buffer [20 mmol of tris/HCl pH 7.5; 3 mmol of $MgCl_2$; 1 mmol of 2-mercaptoethanol; 10% glycerol; 0.01% triton X-100; 0.1 mg/ml of BSA; 11 μM[$\gamma$-$^{32}$P]NTP (0.5 μCi)] (final volume 25 μl). The reaction was stopped by adding 0.5 ml of activated carbon (2 mg/ml). Then, the batch was centrifuged for 10 minutes at 10,000×g, and 50 μl of the supernatant was counted in the scintillation counter (Cerenkov). Substances that influence the NTPase activity of Mater are added to the reaction buffer.

Example 4

Test System for Finding Substances that Prevent the Nucleotide Bond to Mater

The reaction mixture [20 mmol of Tris/HCl pH 7.5; 3 mmol of $MgCl_2$, 1 mmol of 2-mercaptoethanol; 10% glycerol, 0.01% TRITON X-100, 0.1 mg/ml of BSA and 50 μM of [$\gamma$-$^{32}$-P]ATP (0.5 μCi)] with 30–80 pMol of purified Mater protein or a fragment of the Mater protein, which comprises the ATP binding site, was incubated for 30 minutes at 30° C. The reaction was completed by adding ice-cold $NaCl/P_i$, and the samples were microfiltered by BA85 nitrocellulose filter. The nitrocellulose was than washed twice with 2 ml of $NaCl/P_i$, dried, and the bonded [$\gamma$-$^{32}$-P]ATP was counted according to the method of Cerenkov. Substances that influence the binding are added to the reaction mixture.

Example 5

Test System for Finding Substances that Induce Apoptosis (Cell Death Assay)

To find substances that induce apoptosis, the Mater or partial sequences of Mater in a eukaryotic cell, e.g., MCF-7, that was cloned in a eukaryotic expression vector (pCDNA3.1, see Example 1) was transfixed by means of LipfectAMINE (Life Technology, Inc.) according to manufacturer's instructions. 24 hours after the transfection, the cells were set in 0.5% glutaric aldehyde and incubated with 5-bromo-4-chloro-3-indolyl β-D galactopyranosides (X-gal) for 4 hours. The cells were visualized in a phase contrast microscope, and the proportion of apoptotic cells was counted. Substances that influence the apoptosis induction are added to the cell culture medium (10% heat-inactivated fetal calf serum in RPMI 1640).

Sequence Protocol
<110> SCHERING AKTIENGESELLSCHAFT
<120> Human Mater Protein

The entire disclosures of all applications, patents and publications, cited herein and of corresponding German application No. 101 39 874.3-41, filed Aug. 10, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the identification of an effector of a polypeptide, comprising:
    contacting (a) (1) a polypeptide encoded by a nucleotide sequence that hybridizes to the complete complement of SEQ ID NO:1 or 3 under stringent hybridization conditions comprising washing for 1 hour at 68° C. with 1×SSC and 0.1% SDS and which polypeptide possesses nucleoside triphosphatase (NTPase) activity, or (2) a polypeptide fragment of said (1) polypeptide which retains NTPase activity,
    with (b) a test effector, and measuring the NTPase activity of said polypeptide.

2. A method of claim 1, where hydrolyzed NTP is detected.

3. A method of claim 1, where intracellular phosphorylation is detected.

4. A method of claim 1, wherein said test effector is a polypeptide.

5. A method of claim 1, wherein said polypeptide is a (1) polypeptide encoded by a sequence that hybridizes to the complete complement of SEQ ID NO:1 or 3 under stringent hybridization conditions comprising washing for 1 hour with 1×SSC and 0.1% SDS at 68° C. and which polypeptide possesses NTPase activity.

6. A method of claim 1, where said polypeptide is (2) a polypeptide fragment said (1) polypeptide which retains NTPase activity.

7. A method of claim 1, wherein said polypeptide is cell-free.

8. A method for the identification of an effector of a polypeptide, comprising:

contacting (a) a polypeptide of SEQ ID NO: 2 or 4, with (b) a test effector, and measuring the NTPase activity of said polypeptide.

9. A method of claim 8, wherein said polypeptide is a polypeptide of SEQ ID NO: 2.

* * * * *